(12) United States Patent
Johnson

(10) Patent No.: US 7,534,240 B1
(45) Date of Patent: May 19, 2009

(54) NEGATIVE PRESSURE WOUND THERAPY SYSTEM WITH PROVISION FOR INTRODUCTION OF AN AGENT

(75) Inventor: Royce W. Johnson, Universal City, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 09/937,942

(22) PCT Filed: Mar. 31, 2000

(86) PCT No.: PCT/US00/08821

§ 371 (c)(1),
(2), (4) Date: Oct. 2, 2001

(87) PCT Pub. No.: WO00/59424

PCT Pub. Date: Oct. 12, 2000

Related U.S. Application Data

(60) Provisional application No. 60/127,595, filed on Apr. 2, 1999.

(51) Int. Cl.
*A61M 27/00* (2006.01)
*A61F 13/00* (2006.01)

(52) U.S. Cl. .......................... 604/543; 604/304; 602/43

(58) Field of Classification Search .................. 604/313, 604/304–308, 543, 174–176, 289, 40, 24, 604/378; 602/48, 43, 47, 53–54
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby et al. | |

(Continued)

FOREIGN PATENT DOCUMENTS

AU 550575 A1 8/1982

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery, . . .

(Continued)

*Primary Examiner*—Jacqueline F. Stephens

(57) ABSTRACT

A method and apparatus for the introduction to a wound under negative pressure therapy of a wound healing agent, generally comprises a foam pad (11) for insertion substantially into a wound site (12), and a wound drape (13) for sealing enclosure of the foam pad at the wound site. The foam pad is placed in fluid communication with a vacuum source for promotion of fluid drainage. Additionally, the foam pad is predisposed, through grafting or other techniques known to those of ordinary skill in the art, with basic fibroblast growth factor (bFGF), anti-microbial or other factors, also known to those of ordinary skill in the art, for the promotion of increased wound healing.

5 Claims, 1 Drawing Sheet

U.S. PATENT DOCUMENTS

| | | |
|---|---|---|
| 3,367,332 A | 2/1968 | Groves |
| 3,520,300 A | 7/1970 | Flower |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman et al. |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vailancourt |
| 4,533,352 A | 8/1985 | Van Beek et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,769,013 A | 9/1988 | Lorenz et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,100,671 A | 3/1992 | Maeda et al. |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | Debusk et al. |
| 5,344,455 A * | 9/1994 | Keogh et al. ................... 600/36 |
| 5,358,494 A | 10/1994 | Svedman |
| 5,420,197 A | 5/1995 | Lorenz et al. |
| 5,437,622 A | 8/1995 | Carion |
| 5,437,651 A | 8/1995 | Todd et al. |
| 5,466,465 A | 11/1995 | Royds et al. |
| 5,487,889 A | 1/1996 | Eckert et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,662,913 A | 9/1997 | Capelli |
| 5,678,564 A | 10/1997 | Lawrence et al. |
| 5,973,221 A * | 10/1999 | Collyer et al. ................. 602/46 |
| 6,054,504 A | 4/2000 | Dalla Riva Toma |
| 6,071,267 A * | 6/2000 | Zamierowski ............... 604/289 |
| 6,135,116 A | 10/2000 | Vogel et al. |
| 6,142,982 A | 11/2000 | Hunt et al. |
| 6,241,747 B1 | 6/2001 | Ruff |
| 6,287,316 B1 | 9/2001 | Agarwal et al. |
| 6,333,093 B1 | 12/2001 | Burrell et al. |
| 6,345,623 B1 | 2/2002 | Heaton et al. |
| 6,355,858 B1 * | 3/2002 | Gibbins ....................... 602/41 |
| 6,379,702 B1 | 4/2002 | Lorenz et al. |
| 6,398,767 B1 * | 6/2002 | Fleischmann ............... 604/313 |
| 6,458,109 B1 | 10/2002 | Henley et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,645,557 B2 | 11/2003 | Nayan |
| 6,814,079 B2 | 11/2004 | Heaton et al. |
| 7,004,915 B2 | 2/2006 | Boynton et al. |
| 7,005,556 B1 | 2/2006 | Becker et al. |
| 2002/0077661 A1 | 6/2002 | Saadat |
| 2002/0115951 A1 | 8/2002 | Norstream et al. |
| 2002/0120185 A1 | 8/2002 | Johnson |
| 2002/0143286 A1 | 10/2002 | Tumey |
| 2004/0258914 A1 | 12/2004 | Chandra et al. |
| 2006/0029675 A1 | 2/2006 | Ginther |
| 2007/0014837 A1 | 1/2007 | Johnson et al. |
| 2007/0021697 A1 | 1/2007 | Ginther et al. |

FOREIGN PATENT DOCUMENTS

| | | |
|---|---|---|
| AU | 745271 | 3/2002 |
| AU | 755496 | 12/2002 |
| AU | 773002 | 5/2004 |
| CA | 2005436 | 6/1990 |
| CN | 88100913 | 9/1988 |
| DE | 26 40 413 A1 | 3/1978 |
| DE | 43 06 478 A1 | 9/1994 |
| DE | 295 04 378 U1 | 9/1995 |
| EP | 0117632 A2 | 1/1984 |
| EP | 0100148 | 2/1984 |
| EP | 0161865 | 11/1985 |
| EP | 0298726 | 11/1989 |
| EP | 0358 302 | 3/1990 |
| EP | 1 018 967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2333965 A | 8/1999 |
| GB | 2329127 B | 8/2000 |

| | | |
|---|---|---|
| NZ | 514481 | 11/2003 |
| SG | 71559 | 4/2002 |
| WO | WO80/02182 | 10/1980 |
| WO | WO 87/04626 | 8/1987 |
| WO | WO 90/10424 | 9/1990 |
| WO | WO93/09727 | 5/1993 |
| WO | WO94/20041 * | 9/1994 |
| WO | WO/94/20041 | 9/1994 |
| WO | WO96/05873 | 2/1996 |
| WO | WO97/18007 | 5/1997 |
| WO | PCT/GB98/02713 | 9/1998 |
| WO | WO 99/13793 | 3/1999 |
| WO | WO 00/59424 | 10/2000 |
| WO | WO 00/59481 | 10/2000 |
| ZA | 2001/7857 | 6/2004 |

OTHER PUBLICATIONS

Susan Mendez-Eastman, RN; When Wounds Won't Heal, RN Jan. 1998, vol. 61(1); Medical Economics Company, Inc., Montvale, NJ, USA.

James H. Blackburn, II, MD. et al; Negative-Pressure Dressings as a Bolster for Skin Grafts; Annals of Plastic Surgery, vol. 40, No. 5, May 1998, pp. 453-457; . . .

John Masters; Letter to the editor; British Journal of Plastic Surgery, 1998, vol. 51(3), p. 267; Elsevier Science/The British Association of Plastic Surgeons, UK.

S.E. Greer, et al; The Use of Subatmospheric Pressure Dressing Therapy to Clos Lymphocutaneous Fistulas of the Groin; British Journal of Plastic Surgery (2000), 53 . . .

George V. Letsou, M.D., et al; Stimulation of Adenylate Cyclase Activity in Cultured Endothelial Cells Subjected to Cyclic Stretch; Journal of Cardiovascular Surgery, 31, 1990.

Kostyuchenok, B.M, et al. ;Vacuum Treatment in the Surgical Management of Purulent Wounds; Vestnik Khirurgi, Sep. 1986.

Davydov, Yu. A., et al; Vacuum Therapy in the Treatment of Purulent Lactation Mastitis; Vestnik Khirurgi, Sep. 1986.

Yusupov, Yu. N., et al; Active Wound Drainage, Vestnik Khirurgi, vol. 138, Issue 4, 1987.

Davydov, Yu. A., et al; Bacteriological and Cytological Assessment of Vacuum Therapy of Purulent Wounds; Vestnik Khirurgi, Oct. 1988.

Davydov, Yu. A., et al; Concepts For the Clinical-Biological Management of the Wound Process in the Treatment of Purulent Wounds by Means of Vacuum Therapy; Vestnik Khirurgi.

PCT International Search Report; PCT international application PCT/GB98/02713; Jun. 8, 1999.

PCT Written Opinion; PCT international application PCT/GB98/02713; Jun. 8, 1999.

PCT International Examination and Search Report, PCT international application PCT/GB96/02802; Jan. 15, 1998 and Apr. 29, 1997.

PCT Written Opinion, PCT International application PCT/GB/96/02802; Sep. 3, 1997.

International Search Report for PCT international application PCT/GB95/01983; Nov. 23, 1995.

Patent Abstract of Japan; JP4129536; Terumo Corporation; Apr. 30, 1992.

Orringer, Jay, et al; "Management of Wounds in Patients with Complex Enterocutaneous Fistulas", Surgery, Gynecology & Obstertics, Jul. 1987, V. 165, pp. 79-80.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methodsm" Chronic Wound Care, edited by D. Krasner (Health Management Publications, Inc., King of Prussia, PA 1990), pp. 240-246.

G. Živadinović, V. Dukić, D. Radak, and Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

International Search Report and Written Opinion dated Sep. 18, 2008; International Application No. PCT/US07/16815 filed Jul. 26, 2007.

Ambrosio, A. et al.: "V.A.C.® GranuFoam® Silver ™ Dressing, A New Antimicrobial Silver Foam Dressing Specifically Engineered For Use with V.A.C.® Therapy", Kinetic Concepts, Inc. (KCI), Jan. 31, 2006, pp. 1-16.

"Silveron®, Outperforms, Outlasts, Outnumbers, all other silver dressings.", http://www.silverlon.com/body.html, Argentum Medical, LLC, May 9, 2006, p. 4.

"Silveron®, Advanced Antimicrobial Wound, Burn and Surgical Products, What's New", http://www.silverlon.com/press.html, Argentum Medical, LLC, May 9, 2006, p. 5.

Silveron®, Advanced Burn & Wound Care Products (Siverlon versus Acticoat):, http://www.silverlon.com/compare.html, Argentum Medical, LLC, Jul. 7, 2006, p. 5.

"Silveron®, Negative Pressure Wound Devices and Silver Nylon Fabric: A Comparison of Fluid Transfer Capability Utilizing Standard Dressings, Silveron® Contact Dressings and Silveron® Negative Pressure Dressings", http://www.silverlon.com/studies/negative_pressure_dressing.html, Argentum Medical, LLC, Jul. 7, 2006, p. 2.

"Silveron® NPD, Negative Pressure Dressing, Professional Guidelines for Use", http://www.silverlon.com/pressure_dressing_vac.html, Argentum Medical, LLC, Jul. 27, 2006, p. 4.

"Silveron® Antimicrobial Negative Pressure Dressings Designed Spefically for Use with negative Pressure Wound Therapy", http://www.silverlon.com/pressure_dressing_vac.html, Argentum Medical, LLC, Jul. 27, 2006, p. 4.

Silveron® Negative Pressure, Silver Dressings, The most Powerful Antimicrobiral Silver Dressing on the Market:, http://www.silverlon.com/silver_dressing_npwt.html, Argentum Medical, LLC, Jul. 27, 2006, p. 3.

"Silveron®, Better technology. Better outcomes™., Silveron® Wound Contact Dressing, Directions and Protocols for Professional Use", http://www.silverlon.com/wound_dreessing_protocols.html, Argentum Medical, LLC, Jul. 27, 2006, p. 5.

"Silveron®, Better technology. Better outcomes™., Comparative Studies of Combination Therabpy Silveron®/VAC™ alone", http://www.silverlon.com/studies/vac_dressing_combination.html, Argentum Medical, LLC, Jul. 27, 2006, p. 3.

Wound Care Products, Silveron®, Better technology. Better outcomes. ™, http://www.silverlon.com/wound.html, Argentum Medical, LLC, Jul. 27, 2006, p. 5.

"Silveron®, Better technology. Better outcomes.™, Silveron® Wound Dressings Product Descriptions", http://www.silverlon.com/proddetail.html, Argentum Medical, LLC, Jul. 27, 2006, p. 4.

"Burn Care Products, Silveron®, Better technology. Better outcomes. ™", Advanced Silver Antimicrobial Burn Care Products, http://www.silverlon.com/burn.html, Argentum Medical, LLC, Jul. 27, 2006, p. 4.

"Silveron®, Better technology. Better outcomes.™", Advanced Silver Antimicrobial Burn Care Products, Silveron® Burn Dressings, http://www.silverlon.com/burn_product_description.html, Argentum Medical, LLC, Jul. 27, 2006, p. 4.

"Silveron®, Better technology. Better outcomes.™", Advanced Antimicrobial Surgical Dressings, http://www.silverlon.com/cv/cv_silver_wound_dressings.html, Argentum Medical, LLC, Jul. 27, 2006, p. 6.

"Silveron®, Better technology. Better outcomes.™", Advanced Silver Antimicrobial Burn Surgical and Wound Care Products, FDA Marketing Clearances, http://www.silverlon.com/fda.html, Argentum Medical, LLC, Jul. 27, 2006, p. 3.

Non-Final Office Action dated Aug. 5, 2008 for U.S. Appl. No. 11/497,457.

Response filed Nov. 5, 2005 to Non-Final Office Action dated Aug. 5, 2008 for U.S. Appl. No. 11/497,457.

Non-Final Office Action dated Aug. 20, 2008 for U.S. Appl. No. 11/494,171.

Response filed Sep. 18, 2008 to Non-Final Office Action dated Aug. 20, 2008 for U.S. Appl. No. 11/494,171.

New Zealand Examination Report dated Jul. 22, 2008 for New Zealand Application No. 553254.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

Susan Mendez-Eastmen, RN; "When Wounds Won't Heal" RN Jan. 1998, vol. 61 (1); Medical Economics Company, Inc., Montvale, NJ, USA; pp. 20-24.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection - Concerns all Egnell Pumps, Feb. 3, 1983, pp. 2.

Svedman, P.: "Irrigation Treatment of Leg Ulcers", The Lancet, Sep. 3, 1983, pp. 532-534.

* cited by examiner

NEGATIVE PRESSURE WOUND THERAPY SYSTEM WITH PROVISION FOR INTRODUCTION OF AN AGENT

RELATED APPLICATION

This application claims priority to United States provisional application Ser. No. 60/127,595 entitled VACUUM ASSISTED CLOSURE SYSTEM WITH PROVISION FOR INTRODUCTION OF AGENT filed Apr. 2, 1999. By this reference, the full disclosure, including the drawings, of U.S. provisional patent application Ser. No. 60/127,595 is incorporated herein.

TECHNICAL FIELD

The present invention relates to the healing of wounds. More specifically, the present invention relates to the negative pressure therapy of wounds, commercialized as Vacuum Assisted Closure®, or V.A.C.®, by Kinetic Concepts, Inc. of San Antonio, Tex., and wherein a growth factor or other agent is introduced to a wound site through grafting with a pad in order to facilitate wound healing.

BACKGROUND ART

Wound closure involves the inward migration of epithelial and subcutaneous tissue adjacent the wound. This migration is ordinarily assisted through the inflammatory process, whereby blood flow is increased and various functional cell types are activated. Through the inflammatory process, blood flow through damaged or broken vessels is stopped by capillary level occlusion, whereafter cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but are also less able to successfully fight bacterial infection and thus are less able to naturally close the wound. Until recently, such difficult wounds were addressed only through the use of sutures or staples. Although still widely practiced and often effective, such mechanical closure techniques suffer a major disadvantage in that they produce tension on the skin tissue adjacent the wound. In particular, the tensile force required in order to achieve closure using sutures or staples causes very high localized stresses at the suture or staple insertion point. These stresses commonly result in the rupture of the tissue at the insertion points, which can eventually cause wound dehiscence and additional tissue loss.

Additionally, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, methods and apparatus for healing wounds by applying continuous negative pressures have been developed. When applied over a sufficient area of the wound, such negative pressures have been found to promote the migration toward the wound of epithelial and subcutaneous tissues. In practice, the application to a wound of negative pressure, commonly referred to as negative pressure wound therapy (NPWT) and commercialized as Vacuum Assisted Closure®, or V.A.C.®, by Kinetic Concepts, Inc. of San Antonio, Tex., typically involves mechanical-like contraction of the wound with simultaneous removal of excess fluid. In this manner, NPWT therapy augments the body's natural inflammatory process while alleviating many of the known intrinsic side effects, such as the production of edema caused by increased blood flow absent the necessary vascular structure for proper venous return.

While negative pressure wound therapy has been highly successful in the promotion of wound closure, healing many wounds previously thought largely untreatable, some difficulty remains. Because the inflammatory process is very unique to the individual patient, even the addition of negative pressure wound therapy does not result in a fast enough response, especially during the occlusion and initial cleanup and rebuilding stages, for adequate healing of some wounds. It is therefore a principle object of the present invention to provide a method and apparatus whereby the known negative pressure wound therapy modalities are improved through the introduction of growth factors and/or other agents that facilitate wound healing.

DISCLOSURE OF THE INVENTION

In accordance with the foregoing objects, the present invention—a method and apparatus for the introduction to a wound undergoing negative pressure wound therapy of a wound healing agent—generally comprises a foam pad for insertion substantially into a wound site and a wound drape for sealing enclosure of the foam pad at the wound site. According to the invention, the foam pad is placed in fluid communication with a vacuum source for promotion of wound healing. Additionally, the foam pad is predisposed, through grafting or other techniques known to those of ordinary skill in the art, with basic fibroblast growth factor (bFGF), anti-microbials or other factors, also known to those of ordinary skill in the art, for the promotion of increased wound healing.

According to the preferred method of the present invention, a growth factor or other wound healing agent is added to the previously known negative pressure therapy through modification as necessary of the foam pad. Such growth factors as the basic fibroblast growth factor (bFGF) are known to accelerate wound healing due to their potent angiogenesis and granulation tissue formation activities. As has been demonstrated even with difficult to heal wounds, such as infected wounds, burn wounds, and diabetic wounds, the resultant activities lead to the rapid reepithelialization and contraction of the wound. The combination of negative pressure therapy with growth factor introduction, through the modification of the foam pad and predisposition thereof with the bFGF, is therefore thought to be an important contribution to the wound healing arts.

Finally, many other features, objects and advantages of the present invention will be apparent to those of ordinary skill in the relevant arts, especially in light of the foregoing discussions, the following drawing and exemplary detailed description and the claims appended hereto.

BRIEF DESCRIPTION OF THE DRAWINGS

Although the scope of the present invention is much broader than any particular embodiment, a detailed description of the preferred embodiment follows together with an illustrative figure, wherein like reference numerals refer to like components, and wherein.

BEST MODE FOR CARRYING OUT THE INVENTION

Figure 1:
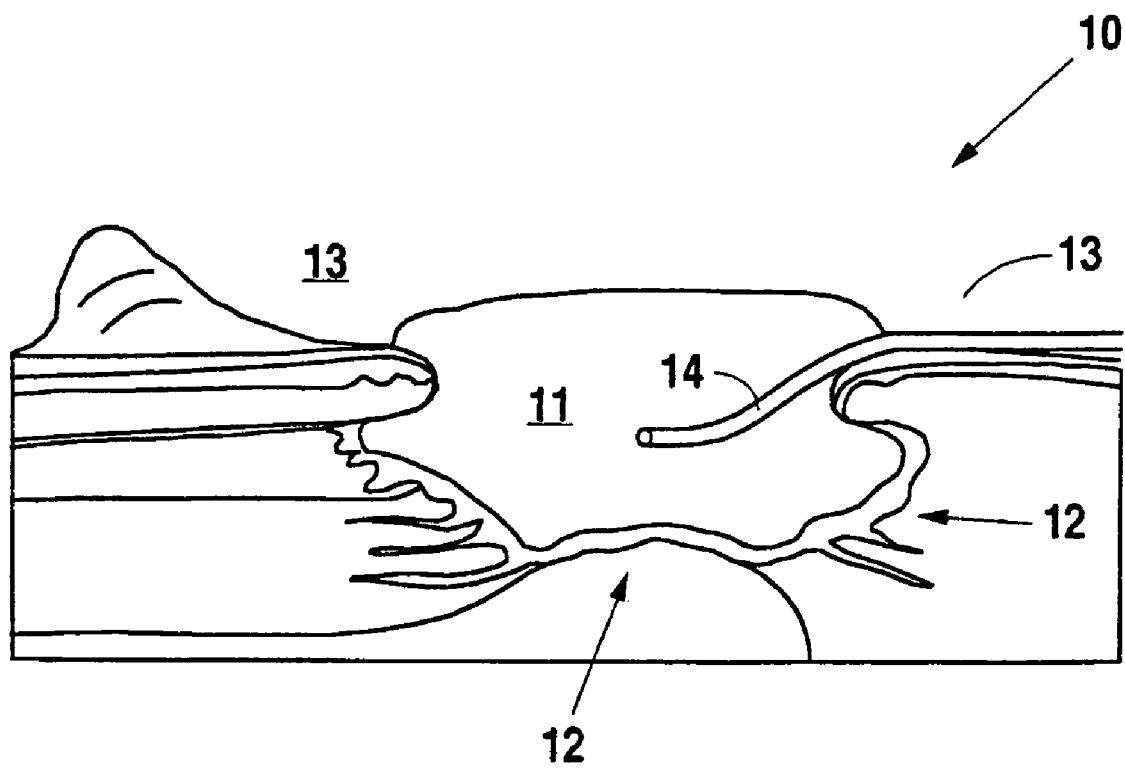
FIG. 1 shows, in partially cut away perspective view, the preferred embodiment of the present invention as applied to a mammalian wound site.

Although those of ordinary skill in the art will readily recognize many alternative embodiments, especially in light of the illustrations provided herein, this detailed description is exemplary of the preferred embodiment of the present invention—wound therapy system with provision for introduction of an agent, the scope of which is limited only by the claims appended hereto.

Referring now to FIG. 1, the present invention 10 is shown to generally comprise a foam pad 11 for insertion substantially into a wound site 12 and a wound drape 13 for sealing enclosure of the foam pad 11 at the wound site 12. According to the invention, the foam pad 11 is placed in fluid communication with a vacuum source for promotion of wound healing. Additionally, the foam pad 11 is predisposed, through grafting or other techniques known to those of ordinary skill in the art, with basic fibroblast growth factor (bFGF), antimicrobials or other factors, also known to those of ordinary skill in the art, for the promotion of increased wound healing.

According to the preferred embodiment of the present invention, the foam pad 11, wound drape 13 and vacuum source are implemented as known in the prior art, each of which is detailed in U.S. patent application Ser. No. 08/517,901 filed Aug. 22, 1995. By this reference, the full disclosure of U.S. patent application Ser. No. 08/517,901 ("the '901 application"), including the claims and drawings, is incorporated herein as though now set forth in its entirety. Additionally, such a negative pressure wound therapy system is readily commercially available through Kinetic Concepts, Inc. of San Antonio, Tex., U.S.A. and/or its subsidiary companies through its V.A.C.® product line.

As detailed in the '901 application, the foam pad 11 preferably comprises a highly reticulated, open-cell polyurethane or polyether foam for good permeability of wound fluids while under suction, but in this application may comprise a conventional sponge cellulose type dressing as necessary for introduction of the desired agent. As also detailed in the '901 application, the foam pad 11 is preferably placed in fluid communication, via a plastic or like material hose 14, with a vacuum source, which preferably comprises a canister safely placed under vacuum through fluid communication, via an interposed hydrophobic filter, with a vacuum pump. Finally, the '901 application also details the wound drape 13, which preferably comprises an elastomeric material at least peripherally covered with a pressure sensitive, acrylic adhesive for sealing application over the wound site 12.

According to the preferred method of the present invention, those components as are described in the '901 application are generally employed as known in the art with the exception that the foam pad 11 of the present invention is modified as necessary for the introduction of a growth factor. Such growth factors as the basic fibroblast growth factor (bFGF) are known to accelerate wound healing due to their potent angiogenesis and granulation tissue formation activities. As has been demonstrated even with difficult to heal wounds, such as infected wounds, burn wounds and diabetic wounds, the resultant activities lead to the rapid reepithelialization and contraction of the wound. The combination of negative pressure therapy with growth factor introduction, though the modification of the foam pad 11 and predisposition thereof with the bFGF, is therefore thought to be an important contribution to the wound healing arts. Likewise, the present method presents an excellent opportunity for the introduction to the wound site 12 of anti-microbial agents, whether alone or in combination with bFGF or other agents.

While the foregoing description is exemplary of the preferred embodiment of the present invention, those of ordinary skill in the relevant arts will recognize many variations, alterations, modifications, substitutions and the like as are readily possible, especially in light of this description, the accompanying drawings and the claims drawn hereto. For example, those of ordinary skill in the art will recognize that while the preferred embodiment of the present invention comprises grafting the desired agent onto the foam pad 11 of the negative pressure therapy system, those of ordinary skill in the art, with the benefit of this exemplary disclosure, will readily recognize many substantially equivalent modes for introduction of the desired agent. For example, in the case of a foam pad 11 that has not been predisposed with an agent or that has been predisposed with an agent which, over time, has subsequently been exhausted into the wound site 12, the desired agent may be injected with a needle and syringe, or the like, through the wound drape 13 and into the foam pad 11. In any case, because the scope of the present invention is much broader than any particular embodiment, the foregoing detailed description should not be construed as a limitation of the present invention, which is limited only by the claims appended hereto.

INDUSTRIAL APPLICABILITY

The present invention is applicable to the wound healing arts.

What is claimed is:

1. A method for promoting wound healing in mammals, said method comprising:
   grafting wound healing factors into a porous pad of a negative pressure system, wherein said negative pressure system comprises:
   the porous pad which is permeable to fluids and adapted for positioning within a sealable space defined in part by a wound surface; and
   a tube having a first end in fluid communication with said porous pad and a second end in fluid communication with a vacuum source, said vacuum source being adapted to apply negative pressure to said porous pad through said tube.

2. The method as recited in claim 1, wherein said wound healing factor comprises basic fibroblast growth factor.

3. The method as recited in claim 1, wherein said wound healing factor comprises an anti-microbial agent.

4. The method as recited in claim 3, wherein said anti-microbial agent comprises an antibiotic.

5. The method as recited in claim 1, said negative pressure system further comprising a wound drape for sealing said porous pad within the sealable space.

* * * * *